United States Patent
Glen et al.

[11] Patent Number: 5,922,748
[45] Date of Patent: Jul. 13, 1999

[54] INDOLE DERIVATIVES AS 5-HT AGONISTS

[75] Inventors: Robert Charles Glen, East Essex; David Lawrence Selwood, Hertofrdshire, both of United Kingdom; Graeme Richard Martin, Palo Alto, Calif.; Christopher James Foster, Stevenage, United Kingdom

[73] Assignee: Glaxo Wellcome Inc., Research Triangle Park, N.C.

[21] Appl. No.: 09/008,833

[22] Filed: Jan. 20, 1998

Related U.S. Application Data

[62] Division of application No. 08/682,615, Oct. 7, 1996, Pat. No. 5,744,466.

[30] Foreign Application Priority Data

Jan. 26, 1994 [GB] United Kingdom ............... 9401436

[51] Int. Cl.⁶ ............ A61K 31/415; C07D 403/04; C07D 403/06
[52] U.S. Cl. ............ 514/385; 514/215; 514/231.1; 514/227.8; 514/241; 514/252; 514/256; 514/266.8; 514/278; 514/337; 514/383; 540/466; 544/6; 544/8; 544/63; 544/88; 544/143; 544/180; 544/238; 544/242; 544/336
[58] Field of Search ............ 548/312.1, 314.7, 548/316.4, 317.1; 514/210, 385, 389, 392, 397, 398

[56] References Cited

U.S. PATENT DOCUMENTS 4,988,703 1/1991 NOrbeck et al. ............ 514/262

FOREIGN PATENT DOCUMENTS

| | | |
|---|---|---|
| 0 313 397 | 4/1989 | European Pat. Off. . |
| 0 366 059 | 5/1990 | European Pat. Off. . |
| WO 91/18897 | 12/1991 | WIPO . |
| WO 94/02477 | 2/1994 | WIPO . |

OTHER PUBLICATIONS

Avram et al Chem. Ber., 1957,1425 1.3–Disubstituierte Cyclobutanderivate.

*Primary Examiner*—Deborah C. Lambkin
*Assistant Examiner*—Jane C. Osuwecki
*Attorney, Agent, or Firm*—Nixon & Vanderhye

[57] ABSTRACT

Compounds of formula (I)

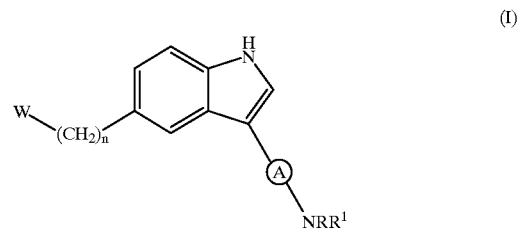

wherein R and $R^1$ are hydrogen, $C_{1-4}$ alkyl or are linked to form a ring,

A is a cycloalkyl or alkyl-cycloalkyl group, n is an integer from 0 to 3,

W is an optionally substituted 5-or 6-membered heterocyclic ring; or W is an optionally substituted aryl, heteroaryl, aryloxy or thiophenoxy group; or W is a group $-SO_2NR^6R^7$ $-NHC(O)R^6R^7$ or $-C(O)NHR^6R^7$; are useful in treating clinical conditions for which a "5-$HT_1$-like" receptor agonist is indicated.

11 Claims, No Drawings

INDOLE DERIVATIVES AS 5-HT AGONISTS

This is a division of application Ser. No. 08/682,615/, filed Oct. 7, 1996, now U.S. Pat. No. 5,744,466.

The present invention is concerned with new chemical compounds, their preparation, pharmaceutical formulations containing them and their use in medicine, particularly the prophylaxis and treatment of migraine.

Receptors which mediate the actions of 5-hydroxytryptanine (5-HT) have been identified in mammals in both the periphery and the brain. Currently, as many as seven 5-HT receptor classes are proposed (Hoyer el al., Pharmacol. Rev., 46, 157–203, 1994), although only the classes nominated 5-HT$_1$, 5-HT$_2$, 5-HT$_3$, and 5-HT$_4$ have established physiological roles. European Patent Specification 0313397 describes a class of 5-HT agonists which act selectively at a particular subtype of 5-HT$_1$ receptor and are effective therapeutic agents for the treatment of clinical conditions in which a selective agonist for this type of receptor is indicated. For example, the receptor in question mediates selective cranial arterial vasoconstriction and inhibition of plasma protein extravasation into the dura mater evoked by activation of the Vth (trigeminal) nerve. The compounds described in the European specification are therefore beneficial in the treatment or prophylaxis of conditions wherein these actions are indicated, for example, migraine, a condition associated with and/or neurogenically-evoked inflammation dilation of the cranial vasculature. However, it is within the scope of the earlier application that the target tissue may be any tissue wherein action is mediated by 5-HT$_1$ receptors of the type referred to above.

EP-A-0486666 discloses a class of compounds having exceptional activity at the 5-HT$_1$ receptor mentioned above and excellent absorption following oral dosing. These properties render the compounds particularly useful for certain medical applications, notably the prophylaxis and treatment of migraine, cluster headache and headache associated with vascular disorders, hereinafter referred to collectively as "migraine".

There has now been discovered a class of compounds which not only demonstrate improved metabolic stability and the necessary 5HT$_1$ receptor agonism, but also display a potentially selective inhibition of neurogenic inflammation and the nerve pathways responsible for the transmission of head pain. The compounds also display partial agonism at the 5HT$_1$ receptor and thus may have reduced side effects compared to previously known 5HT$_1$ receptor agonists.

Thus, according to a first aspect of the present invention there is provided a compound of formula (I):

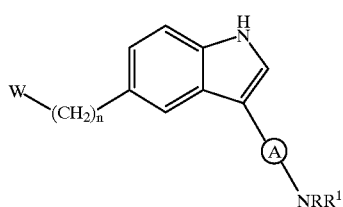

(I)

wherein
R and R$^1$ are each independently hydrogen or C$_{1-4}$ alkyl or R and R$^1$ are linked to form an azetidine ring;
A is C$_{3-6}$ cycloalkyl or C$_{1-3}$ alkyl-C$_{3-6}$ cycloalkyl;
n is an integer of from 0 to 3;
W is a five or six membered ring containing from 1 to 3 hetero atoms independently selected from nitrogen, oxygen, and sulphur, said ring being optionally substituted by one or more substituents independently selected from C$_{1-4}$ alkyl, C$_{3-8}$ cycloalkyl, carbonyl or sulphonyl and optionally said ring is fused to a phenyl ring; or W is an aryl, heteroaryl, aryloxy or thiophenoxy group containing from 1 to 8 carbon atoms said group being optionally substituted by one or more substituents independently selected from C$_{1-4}$ alkyl, phenyl, amino or mono- or di- C$_{1-4}$ alkylamino, and said heteroaryl group containing from 1 to 4 heteroatoms independently selected from nitrogen, oxygen and sulphur, or W is a group —SO$_2$NR$^6$R$^7$—NHC(O)R$^6$R$^7$ or —C(O)NHR$^6$R$^7$ wherein R$^6$ and R$^7$ are independently selected from hydrogen, C$_{1-4}$ alkyl optionally substituted by an aryl group or C$_{1-4}$ alkoxy;

and salts, solvates and physiologically functional derivatives thereof;

with the proviso that said compound is not
3-[cis-1-N,N-dimethylamino)cyclobutan-3-yl]-5-(1,2,4-triazol-1-ylmethyl)-H-indole
or
3-[trans-1-N,N-dimethylamino)cyclobutan-3-yl]-5-(1,2,4-triazol-1-ylmethyl)-H-indole Compounds of formula (I) wherein A is C$_{3-6}$ cycloalkyl are particularly suitable.

Preferably, R and R$_1$ are each independently hydrogen or C$_{1-4}$ alkyl.

In suitable compounds of Formula (I) W is a five or six-membered ring containing from 1 to 3 hetro atoms independently selected from nitrogen, oxygen and sulphur, said ring being optionally substituted by one or more substituents independently selected from C$_{1-4}$ alkyl, C$_{3-8}$ cycloalkyl, carbonyl or sulphonyl and optionally said ring is fused to a phenyl ring; or W is a group SO$_2$NR$^6$R$^7$ wherein R$^6$ and R$^7$ are independently hydrogen or C$_{1-4}$.

Particularly suitable compounds of formula (I) include those wherein:
R and R$^1$ are each independently hydrogen or C$_{1-4}$ alkyl;
A is C$_{3-6}$ cycloalkyl; n is an integer of from 0 to 3;
W is a five or six-membered ring containing from 1 to 3 hetero atoms independently selected from nitrogen, oxygen and sulphur, said ring being optionally substituted by one or more substituents independently selected from C$_{1-4}$ alkyl, C$_{3-8}$ cycloalkyl, carbonyl or sulphonyl and optionally said ring is fused to a phenyl ring; or W is a group SO$_2$NR$^6$R$^7$ wherein R$^6$ and R$^7$ are independently hydrogen or C$_{1-4}$ alkyl; and salts solvates and physiologically functional derivatives thereof;

with the proviso that said compounds are not
3-[cis-1-N,N-dimethylamino)cyclobutan-3-yl]-5-(1,2,4-triazol-1-ylmethyl)-H-indole
or
3-[trans-1-(N,N-dimethylamino)cyclobutan-3-yl]-5-(1,2,4-triazol-1-ylmethyl)-H-indole Compounds of formula (I) wherein A is C$_3$ or C$_4$ cycloalkyl are particularly suitable, with compounds wherein A is C$_4$ cycloalkyl being preferred.

Accordingly, in a second aspect the present invention provides a compound of formula (Ia):

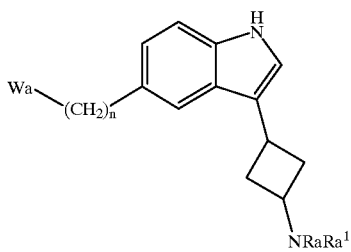

(Ia)

wherein

Ra and Ra¹ are each independently hydrogen or $C_{1-4}$ alkyl; n is an integer of from 0 to 3;

Wa is a five or six membered ring containing from 1 to 3 hetero atoms independently selected from nitrogen, oxygen and sulphur, said ring being optionally substituted by one or more substituents independently selected from $C_{1-4}$ alkyl, $C_{3-8}$ cycloalkyl, carbonyl or sulphonyl and optionally said ring is fused to a phenyl ring, or Wa is a group $SO_2NR^8R^9$ wherein $R^8$ and $R^9$ are independently hydrogen or $C_{1-4}$ alkyl;

and salts, solvates and physiologically functional derivatives thereof;

with the proviso that said compound is not
3-[cis-1-(N,N-dimethylamino)cyclobutan-3-yl]-5-(1,2,4-triazol-1-ylmethyl)-H-indole
or
3-[trans-1-(N,N-dimethylamino)cyclobutan-3-yl]-5-(1,2,4-triazol-1-ylmethyl)-H-indole W in formula (I) or Wa in formula (Ia) includes the following groups (i), (ii), (iii), (iv), (v), (vi), (vii), (viii) or (ix):

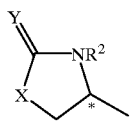

(i)

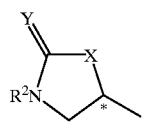

(ii)

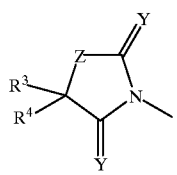

(iii)

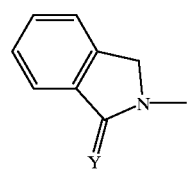

(iv)

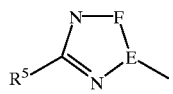

(v)

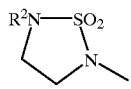

(vi)

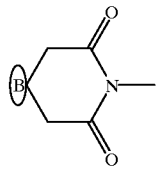

(vii)

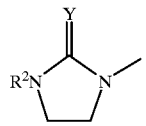

(viii)

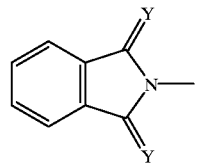

(ix)

wherein $R_2$, $R_3$, and $R_4$, are hydrogen or $C_{1-4}$ alkyl;
$R_5$ is hydrogen or $NR^{10}R^{11}$, wherein $R^{10}$ and $R^{11}$ are hydrogen or $C_{1-4}$ alkyl;
E is —C= or N;
F is N when E is —C= or F is =C— when E is N;
X is —O—, —S—, —NH— or —CH$_2$-;
Y is oxygen or sulphur,
Z is —NH— or —S—; and
B is $C_{3-8}$ cycloalkyl and the chiral centre * in formula (i) or (ii) is in its (S) or (R) form or is a mixture thereof in any proportions;

Suitably X is —O—. Further suitable groups W or Wa are those in which Y is oxygen. Preferred groups W and Wa are those of formulae (i) and (ii). A particularly preferred group W or Wa is that of formula (i) wherein X is —O—, Y is oxygen and $R^2$ is hydrogen.

Examples of preferred compounds of the invention include:
4-[3-(trans-3-aminocyclobutyl)-1H-indol-5-ylmethyl]-(4S)oxazolidin-2-one.
4-[3-(trans-3-aminocyclobutyl)-1H-indol-5-ylmethyl]-(4S)oxazolidin-2-one acetate.
4-[3-(cis-3-aminocyclobutyl)-1H-indol-5-ylmethyl]-(4S)oxazolidin-2-one acetate.
4-[3-(trans-3-dimethylaminocyclobutyl)-1H-indol-5-ylmethyl]-(4S)oxazolidin-2-one.
5-(5,5-dimethyl)-3-{2-[3-trans-3-dimethylaminocyclobutyl)-1H-indol)-5-yl]ethyl}imidazolidin-2,4-dione
3-{2-[3-trans-3-dimethylaminocyclobutyl)-1H-indol-5-yl]ethyl}imidazolidin-2,4-dione.

3-{2-[3-(trans-3-aminocyclobutyl)-1H-indol-5-yl]ethyl}-5,5-dimethylimidazolidin-2,4-dione.

2-{2-[3-(trans-3-dimethylaminocyclobutyl)-1H-indol-5-yl]ethyl}phthalamide.

3-{2-[3-(trans-3-dimethylaminocyclobutyl)-1H-indol-5-yl]ethyl}-3-azaspiro[5,5]undecane-2,4-dione.

N-methyl-[3-(trans-3-dimethylaminocyclobutyl)-1H-indol-5-yl]methanesulphonamide.

4-[3-(trans-3-dimethylaminocyclobutyl)-1H-indol-5-ylmethyl]-(4R)oxazolidin-2-one.

4-[3-(trans-3-dimethylaminocyclobutyl)-1H-indol-5-ylmethyl]-3-methyl(4S)-oxazolidin-2-one.

5,5-dimethyl-3-[3-(trans-3-dimethylaminocyclobutyl)-1H-indol-5-ylmethyl]imidazolidin-2,4-dione.

3-[3-(trans-3-dimethylaminocyclobutyl)-1H-indol-5-ylmethyl]imidazolidin-2,4-dione.

5-[3-(trans-3-dimethylaminocyclobutyl)-1H-indol-5-ylmethyl]oxazolidin-2-one.

4-[3-(trans-3dimethylaminocyclobut-1-ylmethyl)-1H-indol-5-ylmethyl]-(4S)oxazolidin-2-one.

4-[3-(trans-3-methylaminocyclobutyl)-1H-indol-5-ylmethyl]-(4S)oxazolidin-2-one.

4-[3-(trans-3-dimethylaminocyclobutyl)-1H-indol-5-ylmethyl]-3-methyl(4R)oxazolidin-2-one.

3-(trans)-3-dimethylaminocyclobutyl)-1H-indol-5-yl acetamide.

4-[3-(cis-3-dimethylaminocyclobutyl-1H-indol-5ylmethyl]-(4S)oxazolidin-2-one.

5-phenoxy-3-(trans-3-aminocyclobutyl)-1H-indole.

5-phenoxy-3-(trans-3-dimethylaminocyclobutyl)-1H-indole.

N-benzyl-3-(trans-3-dimethylaminocyclobutyl)-1H-indol-5-yl acetamide.

5-N-benzylcarboxamido-3-(trans-3-dimethylaminocyclobutyl)-1H-indole.

3-methyl-5-[3-(trans-3-dimethylaminocyclobutyl)indol-5-yl]-1,2,4-oxadiazole.

3-methyl-5-[3-(trans-3-dimethylaminocyclobutyl)indol-5-ylmethyl]-1,2,4-oxadiazole.

3-methyl-5-[3-trans-3-dimethylamninocyclobutyl)indol-5-ylmethyl]-1,2,4-triazole.

(S)-2-(5-(2-Oxo-4-oxazolidinylmethyl)-1H-indol-3-yl) cyclopropylamine.

5-carboxamido-3-(trans-3-dimethylaminocyclobutyl)-1H-indole.

Physiologically acceptable salts are particularly suitable for medical applications because of their greater aqueous solubility relative to the parent, ie basic, compounds. Such salts must clearly have a physiologically acceptable anion. Suitable physiologically acceptable salts of the compounds of the present invention include those derived from acetic, hydrochloric, hydrobromic, phosphoric, malic, maleic, fumaric, citric, sulphuric, lactic, or tartaric acid. The succinate and chloride salts are particularly preferred for medical purposes. Salts having a non-physiologically acceptable anion are within the scope of the invention as useful intermediates for the preparation of physiologically acceptable salts and/or for use in non-therapeutic, for example, in vitro situations.

According to a third aspect of the present invention, there is provided a compound of formula (I) or (Ia) or a physiologically acceptable salt, solvate, or physiologically functional derivative thereof for use as a therapeutic agent, specifically as a "5-HT$_1$-like" receptor agonist, for example, as a carotid vasoconstrictor or as an inhibitor of neurogenic inflammation in the prophylaxis and treatment of migraine. As indicated, however, target organs for the present compounds other than the carotid vasculature are within the scope of the present invention.

The amount of a compound of formula (I) or (Ia), or a salt or solvate thereof which is required to achieve the desired biological effect will depend on a number of factors such as the specific compound, the use for which it is intended, the means of administration, and the recipient. A typical daily dose for the treatment of migraine may be expected to lie in the range 0.01 to 5 mg per kilogram body weight. Unit doses may contain from 1 to 100 mg of a compound of formula (I) or,(Ia), for example, ampoules for injection may contain from 1 to 10 mg and orally administrable unit dose formulations such as tablets or capsules may contain from 1 to 100 mg. Such unit doses may be administered one or more times a day, separately or in multiples thereof. An intravenous dose may be expected to lie in the range 0.01 to 0. 15 mg/kg and would typically be administered as an infusion of from 0.0003 to 0.15 mg per kilogram per minute. Infusion solutions suitable for this purpose may contain from 0.01 to 10 mg/ml.

When the active compound is a salt or solvate of a compound of formula (I) the dose is based on the cation (for salts) or the unsolvated compound.

Hereinafter references to "compound(s) of formula (I) or (Ia)" will be understood to include physiologically acceptable salts and solvates thereof.

According to a fourth aspect of the present invention, therefore, there are provided pharmaceutical compositions comprising, as active ingredient, at least one compound of formula (I) or (Ia) and/or a pharmacologically acceptable salt or solvate thereof together with at least one pharmaceutical carrier or excipient. These pharmaceutical compositions may be used in the prophylaxis or treatment of clinical conditions for which a "5-HT$_1$-like" receptor agonist is indicated, for example, migraine. The carrier must be pharmaceutically acceptable to the recipient and must be compatible with, i.e. not have a deleterious effect upon, the other ingredients in the composition. The carrier may be a solid or liquid and is preferably formulated with at least one compound of formula (I) or (Ia) as a unit dose formulation, for example, a tablet which may contain from 0.05 to 95% by weight of the active ingredient. If desired, other physiologically active ingredients may also be incorporated in the pharmaceutical compositions of the invention.

Possible formulations include those suitable for oral, buccal parenteral (for example, subcutaneous, intramuscular, or intravenous), rectal, topical and intranasal administration. The most suitable means of administration for a particular patient will depend on the nature and severity of the condition being treated and on the nature of the active compound, but, where possible, oral administration is preferred.

Formulations suitable for oral administration may be provided as discrete units, such as tablets, capsules, cachets, or lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically, a flavoured base, such as sugar and acacia or tragacanth, and pastilles comprising the active compound in an inert base, such as gelatin and glycerin or sucrose and acacia.

Formulations suitable for parenteral administration typically comprise sterile aqueous solutions containing a predetermined concentration of the active compound; the solution is preferably isotonic with the blood of the intended recipient. Although such solutions are preferably administered intravenously, they may also be administered by subcutaneous or intramuscular injection.

Formulations suitable for rectal administration are preferably provided as unit-dose suppositories comprising the active ingredient and one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethylene glycols, alcohols, and combinations thereof. The active ingredient is typically present in such formulations at a concentration of from 0.1 to 15% w/w.

The formulations of the invention may be prepared by any suitable method, typically by uniformly and intimately admixing the active compound(s) with liquids or finely divided solid carriers, or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by moulding an intimate mixture of powdered active ingredient and inert liquid diluent.

Aqueous solutions for parenteral administration are typically prepared by dissolving the active compound in sufficient water to give the desired concentration and then rendering the resulting solution sterile and isotonic.

Thus, according to a fifth aspect of the present invention, there is provided the use of a compound of formula (I) or (Ia) in the preparation of a medicament for the prophylaxis or treatment of a clinical condition for which a "5-HT$_1$-like" receptor agonist is indicated, for example, migraine.

According to a sixth aspect, there is provided a method for the prophylaxis or treatment of a clinical condition in a mammal, for example, a human, for which a "5-HT$_1$-like" receptor agonist is indicated, for example, migraine, which comprises the administration to said mammal of a therapeutically effective amount of a compound of formula (I) or (Ia) or of a physiologically acceptable salt, solvate, or physiologically functional derivative thereof.

In a further aspect the invention provides a process for the preparation of compound of formula (I) by reacting a compound of formula (II)

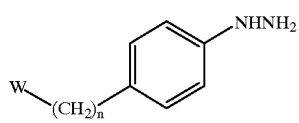

(II)

wherein n and W are as hereinbefore defined, with a compound of formula (III)

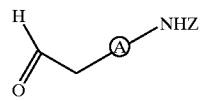

(III)

wherein A is as hereinbefore defined and Z is a benzyloxycarbonyl group, to give a compound of formula I wherein R and R$^1$ are both hydrogen. The reaction is typically carried out by heating the compounds at a non-extreme temperature suitably in the range 50 to 100° C. and preferably at about 80° C. in the presence of an aqueous mineral acid e.g. sulphuric acid and then removing the benzyloxycarbonyl group by refluxing in a polar solvent system, for example formic acid in methanol in the presence of a catalyst such as palladium on carbon.

Compounds of formula (Ia) can be prepared by reacting a compound of formula (II) wherein W is Wa with a compound of formula (III) wherein A is cyclobutyl.

Standard N-alkylation methods may be used to convert compounds of formula (I) or (Ia) wherein R and R$^1$ are hydrogen to corresponding compounds wherein R and/or R$^1$ are C$_{1-4}$ alkyl.

Compounds of formula (I) or (Ia) wherein R=R$^1$=C14 alkyl may be prepared from the corresponding compound wherein R=R$^1$=H by methods of N, N-dialkylation well known to those skilled in the art, for example, by treatment with the appropriate aldehyde in the presence of a reducing system, for example, sodium cyanoborohydride acetic acid, in a polar solvent, such as methanol.

Compounds of formula (I) or (Ia) wherein R or R$^1$=C$_{1-4}$ alkyl may be prepared from the corresponding compound wherein R=R$^1$=H by N-benzylation using benzaldehyde and a suitable reducing agent, for example sodium borohydride, in a polar solvent such as ethanol, followed by N-alkylation using a suitable agent, such as the appropriate dialllylsulphate, typically in the presence of a base, for example anhydrous potassium carbonate, in a polar aprotic solvent, such as DMF, and finally N-debenzylation typically by catalytic hydrogenation using, for example Pd/C in a polar solvent such as ethanol.

Compounds of formula (III) may be prepared from the appropriate 3-methylenecyclopalkane-1-carboxylic acid (J.Amer.Chem.Soc. 1959, 81, p2723) by reaction with diphenylphosphoryeazidate and benzyl alcohol as described in EP-A-0366059. Alternatively t-butyl alcohol, or 4-nitrobenzyl alcohol may be used. The reaction may be carried out in an aromatic solvent e.g. toluene, benzene, xylene or pyridine. Chlorinated solvents such as chloroform and 1,2-dichloroethane, and polar aprotic solvents, such as glyme and dimethylformmde are also suitable. The intermediate carbamate may also be prepared by reaction of the aforementioned acid to form the corresponding acyl azide and rearrangement to form the isocyanate. This isocyanate may then be reacted with an alcohol to form the carbamate.

Compounds of formula (III) are prepared from the intermediate carbamates by a hydroformylation reaction (also known as the Oxo reaction) with hydrogen gas and carbon monoxide gas in the presence of a suitable transition metal catalyst. Rhodium, ruthenium, cobalt or platinum catalysts may be used. Chlorotris (triphenylphosphine) rhodium (I) and carbonylhydridotris (triphenylphosphine) rhodium (I) are preferred catalysts. Suitable pressures of hydrogen are in the range 1–100 atmospheres and a pressure of approximately 20 atmospheres is preferred. The pressure of carbon monoxide is suitably in the range 1–100 atmospheres and is preferably approximately 10 atmospheres. The hydroformylation reaction may be carried out in an aromatic solvent, e.g. toluene, xylene or benzene; a non-aromatic hydrocarbon, e.g. hexane, heptane or petroleum fraction; or in a dipolar aprotic solvent such as dimethyl formamide. Toluene is the preferred solvent. The reaction can be carried out at a non-extreme temperature, suitably in the range 20–100° C., and is preferably carried out at approximately 70° C.

Compounds of formula (III) are believed to be novel and accordingly, in an eighth aspect, the present invention provides novel intermediates of formula (III).

Hydrazines of formula (II) may be prepared according to the methods of *Cripps et. al. J Amer. Chem. Soc.* 81 (1959) p2723 and as described in EP-A-0486666. Further methods for preparing these hydrazines are described in the Examples hereafter.

For hydrazines of formula (II) wherein W is a group of formula (v)

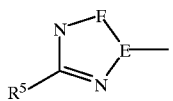

the heterocyclic moiety may be constructed using the methodology described in Lin et. al., *J Org. Chem.*, (1979), 44, p4160–4164.

A typical reaction scheme for the preparation of a compound of formula (I) is as follows:

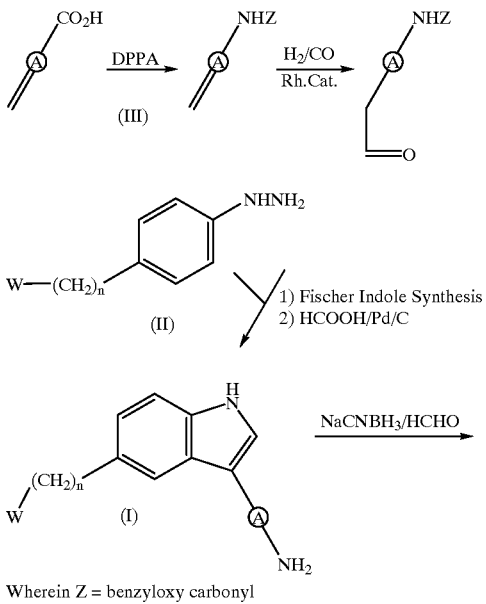

Wherein Z = benzyloxy carbonyl

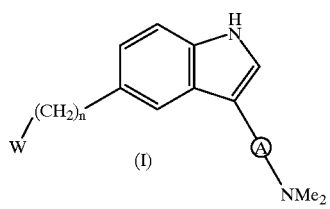

An alternative route for synthesising compounds of formula (I) or (Ia) is by reacting a compound of formula (II) with a compound of formula (IV)

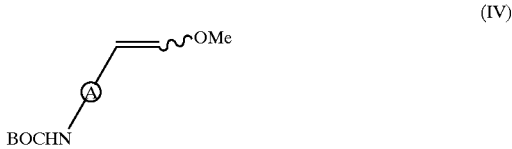

wherein BOC represents a tertiary butoxycarbonyl group, to give a compound of formula (I) wherein $R=R^1=H$ and optionally converting that compound into a compound of formula (I) wherein R and/or $R^1=C_{1-4}$ alkyl by standard alkylation techniques as hereinbefore described.

The reaction is suitably carried out in the presence of an aqueous mineral acid e.g. sulphuric acid at a non-extreme temperature, typically in the range 50 to 100° C. and preferably at about 80° C.

Compounds of formula (IV) may be prepared as follows. An amide of formula (X)

can be prepared by coupling the known 3-benzyloxycycloalkane-1-carboxylic acid *M. Maxim* et al. *Chem. Ber.* 1957, 90, 1425 with N,O-dimethylhydroxylamine hydrochloride either via the acid chloride or by the use of amide coupling agents such as dicyclohexyl carbodimide, N,N'-carbonyl diimidazole or diphenyl phosphoroazidate. The coupling may also be effected by the use of an activated ester or by means of a mixed anhydride. The use of the acid chloride is preferred. The acid chloride may be prepared by using thionyl chloride, phosphorus pentachloride or oxaloyl chloride, but thionyl chloride is preferred. Suitable solvents for the coupling include pyridine, toluene or acetronitrile or chlorinated solvents such as dichloromethane in the presence of a base e.g. pyridine. Dichloromethane is preferred.

An amine of formula (IX)

can be prepared from the compound of formula (X) by hydrogenolysis of the benzyloxy group using a transition metal catalyst and a source of hydrogen to form an intermediate alcohol. This alcohol is converted into a leaving group, for example by conversion into its tosylate or mesylate derivative, and is then reacted with a source of azide ion to form the azide. Reduction of the azide using a transition metal catalyst and a source of hydrogen forms the amine of formula (IX).

Typical catalysts for the hydrogenolysis step include palladium on carbon, palladium hydroxide on carbon, palladium black and platinum oxide. Palladium hydroxide on carbon is preferred. Suitable sources of hydrogen include hydrogen gas at 1 to 100 atmospheres pressure, ammonium formate and formic acid. The preferred source of hydrogen is hydrogen gas at 15 atmospheres. The reaction is suitably carried out in an organic solvent such as ethanol, methanol, ethyl acetate or acetic acid and is preferably carried out in ethanol.

Formation of the tosylate or mesylate derivative may be effected using p-toluenesulphonyl chloride or methanesulphonyl chloride in the presence of a base such as pyridine, triethylamine or 4-dimethylaminopyridine. Suitable solvents include pyridine, dichloromethane and toluene. The use of p-toluenesulphonyl chloride in pyridine is preferred.

Sodium azide is the preferred source of azide ion and the reaction is suitably carried out in a polar aprotic solvent e.g. dimethylformamide, dimethyl sulphoxide or N-methylpyrrolidinone at an elevated temperature suitably in the range of 40–170° C. Preferably, the reaction is carried out in dimethylformamide at approximately 80° C.

Reduction of the azide is effected by the use of a transition metal catalyst such as palladium on carbon, palladium hydroxide on carbon, palladium black or platinum oxide in a suitable solvent e.g. an alcohol such as ethanol or methanol containing a mineral acid such as hydrochloric acid or an organic acid such as acetic acid. Sources of hydrogen include hydrogen gas at 1 to 100 atmospheres pressure, ammonium formate and formic acid. The reduction is preferably carried out using palladium hydroxide on carbon in ethanol containing acetic acid under 1 atmosphere of hydrogen.

The t-butyloxycarbonyl-enol ether of formula (IV) is prepared from the amine of formula (IX) by protecting the amine group, for example as its t-butyloxycarbonyl derivative, using a suitable reagent. The N,N'-dimethylhydroxylamide moiety is then reduced to the aldehyde using a hydride reducing agent. Wittig reaction of the aldehyde with a suitable reagent gives the compound of formula (IV).

The protection stage can be effected using reagents such as dithutyldicarbonate or N-'butoxycarbonyloxy) succinimde in the presence of a solvent. Suitable solvents are organic solvents such as dichloromethane, toluene and dioxane. The reaction is typically carried out in the presence of an amine catalyst such as 4-dimethylaminopyridine.

The reduction of the N,N'-dimethylhydroxylamide moiety is typically carried out using, for example, lithium aluminium hydride, which is preferred, or dihsobutylaluminium hydride in an organic solvent. Suitable solvents include toluene, tetrahydrofuran and diethylether. Tetrahydrofuran is the preferred solvent and the reduction is preferably carried out at a temperature of approximately 0° C.

The Wittig reaction is carried out using, for example, methoxymethyltriphenylphos phonium bromide in the presence of a strong base but methoxymethyltriphenylphosphonium bromide and strong base is preferred. Suitable bases are n-butyl lithium, sodium hydride, sodium amide or potassium 'butoxide, which is preferred. The reaction is typically carried out in a solvent. Suitable solvents are etheral solvents, e.g. tetrahydrofuran or glyme, or polar apotic solvents such as dimethylformamide. Tetrahydrofuran is the preferred solvent and the reaction is suitably carried out at 0–100° C. and preferably at approximately 80° C.

Intermediates of formula (IV) are believed to be novel and accordingly in a further aspect, the present invention provides compounds of formula (IV).

Compounds of formula (Ia) are prepared by reacting a compound of formula (IV) wherein A is cyclobutyl with a compound of formula (II) wherein W is Wa.

A typical reaction scheme is as follows

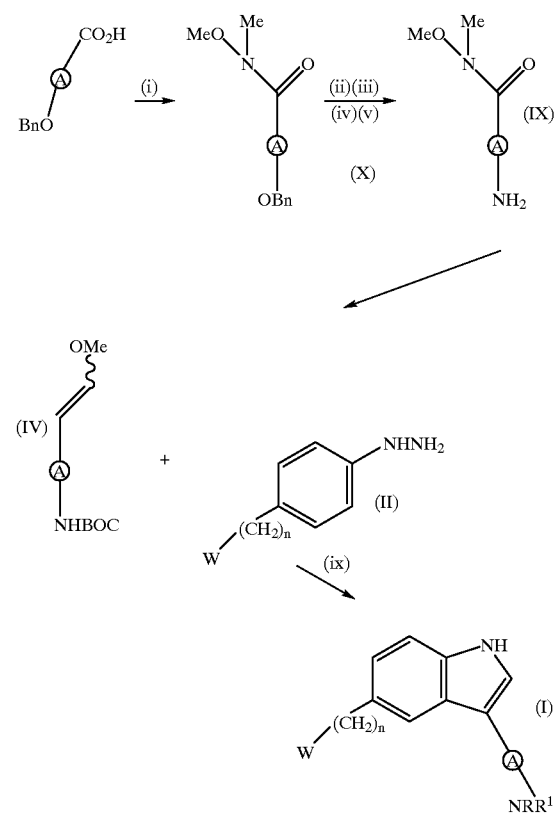

Reagents; (i) $SOCl_2/HN(OMe)Me$, (ii) $Pd/C/H_2$, (iii) TsCl/pyridine, (iv) $NaN_3/DMF$; (v) $Pd/C/H_2$; (vi) $(BOC)_2O$; (vii) $LiAlH_4$; (viii) $Ph_3PCH_2OMe/KO^tBu$; (ix) AcOH 25% eq.

Compounds wherein A is a cyclopropyl group can suitably be prepared by reacting a compound of formula (V)

(V)

wherein BOC represents a tertiary butoxy carbonyl group with a hydrazine of formula (II).

Intermediates of formula (V) are believed to be novel and accordingly, in a further aspect, the present invention provides compounds of formula (V).

A typical reaction scheme is as follows:

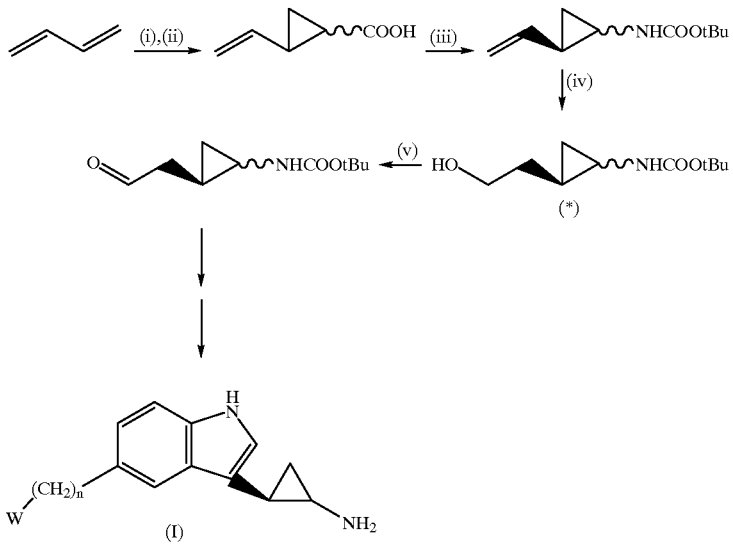

Reagents: (i) $N_2CHCO_2Et/(RhOAc)_2$, (ii) $KOH/H_2O$, (iii) DPPA/tBuOH/PHMe, (iv) $BH_3/THF/H_2O_2/OH$-, (v) $DMSO/(COCl)_2$ The aldehyde of formula (V) may be prepared by oxidation of the alcohol (*). Although this alcohol has been described in U.S. Pat. No. 4,988,703, no indication as to stereochemistry has previously been. We have now discovered methods whereby the alcohol (*) may be prepared in its pure trans form. Thus, Curtius reaction of 2-ethylenecyclopropane carboxcylic acid, according to the methods described above for the preparation of compounds of formula (III), gives the carbamate product. In this case, the preferred alcohol is t-butylalcohol and trans-N-t-butoxycarbonyl-2-ethenylcyclopropylamine is isolated.

The trans-ethenyl compound so isolated is now converted into the terminal alcohol by a hydroboration reaction with oxidation of the intermediate borane by hydrogen peroxide. Typical reagents include borane-solvent complexes, or sodium borohydride boron trifluoride etherate. The use of borane-tetrahydrofuran complex in tetrahydrofuran is preferred. Oxidation of the alcohol (*) to the aldehyde (V) may be effected by organic or inorganic oxidants. Organic oxidants include oxalylchloride/dimethylsulphoxide, inorganic oxidants include chromium, manganese and molybdenum complexes. Mixed organic/catalyst systems such as N-methyl-morpholine-N-oxide/tetrapropylammonium perruthenate are also suitable. The preferred oxidant system is oxalylchloride/dimethylsulphoxide (known as the Swern oxidation). Suitable solvents include chlorinated and non-chlorinated organic solvents. Dichloromethane is preferred.

An alternative scheme for the synthesis of compounds of formula (I) or (Ia) wherein one of R or $R^1$ is hydrogen with the other being $C_{1-4}$ alkyl is as follows:

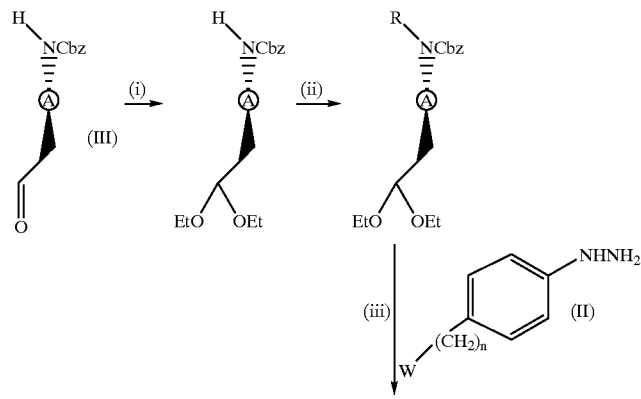

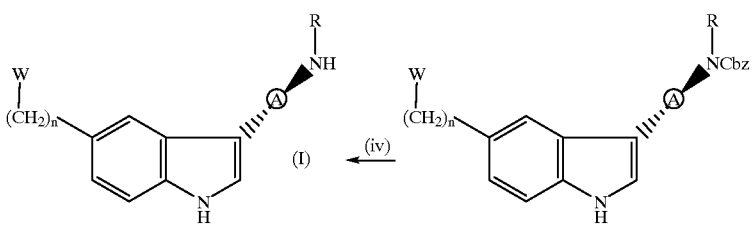

Reagents: (i) (EtO)₃CH/pTsOH, (ii) NaH/RI, (iii) 1%H₂SO₄/80°, (iv) Pd(OH)₂/10%HCOOH/MeOH reflux The invention will now be described, by way of illustration only by the following examples:

The aldehyde of formula (III) may be protected as a dialkyl acetal derivative where the alkyl group may be $C_1$–$C_5$ and may be alicyclic or cyclic. The diethylacetal is preferred. The protection may be effected by reagents such as trialkylorthoformates or dialkoxypropanes in the presence of an acid catalyst such as organic or mineral acids or Lewis acids. Triethylorthoformate in the presence of p-toluene sulphonic acid is preferred.

The acetal may be alkylated using a base and a suitable alkylating agent. Suitable alkylating agents include alkyl halides, alkylsulphonates or dialkylsulphates. Methyl iodide is the preferred alkylating agent. Suitable solvents for the reaction include polar aprotic solvents, etheral solvents and alcohols. Dimethyformamide is preferred. The alkylated acetal may now be reacted with a hydrazine of formula (II) as described above and the carbamate protecting group removed to give the monoalkylated product.

EXAMPLE 1

4-[3-(trans-3-aminocyclobutyl)-5-indolylmethyl)-(4S)-oxazolidin-2-one and 4-[3-(cis-3-aminocyclobutyl)-5-indolymethyl)-(4S)-oxazolidin-2-one acetate.

(a) cis and trans N-Methoxy-N-methyl-3-benzyloxycyclobutane-1-carboxamide (1)

To 3-benzyloxy cyclobutane-1-carboxylic acid (8.23 g, 39.95 mmol) was added thionyl chloride (50 ml) and dimethyl formamide (2 drops). The reaction was refluxed for 2h then the thionyl chloride removed on a rotary evaporator. The acid chloride was dissolved in dichloromethane (50 ml) and cooled to 0° C. The N, O-dimethyl hydroxylamine hydrochloride (4.29 g, 44 mmol) was followed by pyridine 9.71 g, 100 mmol). The reaction was allowed to warm to r.t. and stirred overnight. The volatiles were removed on a rotary evaporator and the residue taken up in 10% aq. hydrochloric acid and extracted with ethylacetate. The extracts were washed with water and dried over sodium sulphate.

Column chromatography gave the product (7.7 g, 31 mmol, 77%) as a clear oil. HRMS for $C_{14}H_{19}NO_3$, calculated 249.13649 found 249.1354.

(b) cis and trans 3-hydroxy-N-methoxy-N-methyl cyclobutane-1-carboxamide.

The benzyl ether (7.7. g, 30.9 mmol) in ethanol (250 ml) was hydrogenated over 10% palladium hydroxide on carbon (1 g) at 15 atm $H_2$. The product was purified by column chromatography to give 4.02 g, 25.2 mmol, 82%. HRMS for $C_7H_{13}NO_3$, calculated 159.08954 found 159.0892.

(c) cis and trans 3-Azido-N-methoxy-N-methylcyclobutane-1-carboxamide

To the alcohol (4.02 g, 25.2 mmol) in pyridine (40 ml) at 0° C. was added the p-toluensulphonychloride (5.29 g, 27.7 mmol) and the reaction stirred for 16 hrs. The volatiles were removed on a rotary evaporator and the residue taken up in ethyl acetate (150 ml) and washed with 3% aq. hydrochloric acid in sat. brine (2×100 ml), sat. aq sodium bicarbonate (50 ml) and dried over sodium sulphate. Chromatography gave 7.47 g, 23.1 mmol, 92% of tosylated compound which was used directly for the next stage.

To the tosylate in dimethylformamide (40 ml) was added the sodium azide (1.49 g, 23 mmol) and the reaction heated to 80° C. for 4 h. An additional amount of sodium azide (0.75 g, 11.5 mmol) was added and heating continued for 2 hr. The cooled reaction was poured into water (200 ml) and extracted with ethyl acetate. The extracts were dried over sodium sulphate. Column chromatography gave the product (4.1 g, 22.3 mmol, 88%) as an oil. HRMS for $C_7H_{12}O_2$; calculated 184.09603 found 184.977.

(d) cis and trans 3-Amino-N-methoxy-N-methylcyclobutane-1-carbonamide

The azide (4.1 g, 22.3 mmol) in ethanol (60 ml) and acetic acid (2 ml) was hydrogenated (1 atm $H_2$) over 10% palladium on carbon (100 mg). Column chromatography gave the product (1.28 g, 8:1 mmol, 36%) as an oil. HRMS for $C_7H_{12}N_2O_2$; calculated 158.10553 found 158.1033.

(e) cis and trans 3-$^t$ butoxycarbonylamino-N-methoxy-N-methyl-1-cyclobutane carboxamide To the amine (1.28, 8.1 mmol) and 4-dimethyl aminopyridine in dichloromethane (20 ml) was added di $^t$ butylcarbonate (3.54 g, 16.2 mmol) in one portion and the reaction stirred for 16 hr. Water (50 ml) was added and the reaction stirred for 30 min. The dichloromethane was separated and dried over sodium sulphate. Column chromatography gave the product as an oil (1.46 g, 5.66 mmol, 70%). Microanalysis calculated C 55.81, H 8.53, N 10.85, found C55.62, H 8.87. N 10.49.

(f) cis and trans 3-t butoxycarbonylamino-cyclobutane-1-carboxaldehyde

To the methoxymethylamide (258 mg, 1 mmol) in tetrahydrofuran (5 ml) at −50° C. was added di isobutyl aluminium hydride (1.1 mol of a 1M solution in toluene) and the reaction allowed to warm to 0° C. for 30 min, then water (20 ml) added. The mixture was extracted with ethyl acetate and the extracts dried over sodium sulphate. Column chromatography gave the pure product. Microanalysis calculated C 60.30, H 8.84, N 7.04 found C 60.30, H 8.87, N 7.02.

(g) cis and trans N-t butoxycarbonyl-3-(2-methoxyethenyl) cyclobutane-1-amine.

To methoxymethyltriphenyl phosphonium bromidelsodium amide (0.23 mmol) was added tetrahydrofuran (5 ml) and the reaction stirred for 30 min. The aldehyde (30 mg, 0.151 mmol) in tetrahydrofuran (0.5 ml) was added dropwise and the reaction heated to 80° C. for 4 hr. The cooled reaction mixture was poured into water (20 ml) and extracted with ethyl acetate (2×20 ml). The extracts were dried over sodium sulphate. Column chromatography gave the product. (14.3 mg, 0.063 mmol, 42%) as an oil.

(h) 4-[3-(trans-3-aminocyclobutyl)-5-indolylmethyl)-(4S)-oxazolidin-2-one acetate, and 4-[3-(cis-3-aminocyclobutyl)-5-indolymethyl]-(4S)-oxazolidin-2-one acetate.

To the appropriate hydrazine (310 mg, 1.5 mmol) in 1% aq sulphuric acid (10 ml) was added the methylphenol ether (~1 mmol) and the reaction heated to 80° C. for 6 hrs. The reaction was cooled and washed with ethyl acetate. The acidic layer was saturated with sodium chloride and extracted with tetrahydrofuran. The extracts were dried over sodium sulphate. Column and HPLC chromatography gave the trans product (gum) HRMS calculated for $C_{16}H_{19}N_3O_2$ 285.14773 found 285.1477 and the cis product mpt 180–181° C. HRMS calculated 285.14773 found 285.1458.

EXAMPLE 2

Trans-4-[3-(3-(dimethylaminocyclobutyl)-5-indolylmethyl]-(S)-1,3 oxazolidin-2-one (a) Trans-N-(benzyloxy carbonyl)-cyclobutanamine-3-acetaldehyde Trans-N-(benzyloxycarbonyl)-3-methylenecyclobutanamine (18 g, 83 mmol)(prepared as described in EP-A-0366059) and tris(triphenylphosphine) rhodium chloride (400 mg 0.43 mmol) were heated to 70° C. in toluene (250 ml) under 100 atmospheres of $CO:H_2$ (1:1 mixture for 18 hrs. The solvent was evaporated under reduced pressure and the residue chromatographed on silica eluting with 25% ethylacetate in cyclohexane. First product eluted (r.f.~0.25) mixture of cis and trans branched chain aldehydes. Second product eluted (r.f.~0.1) mixture of cis and trans straight chain aldehydes. The trans isomer was crystallised from ether as white needles (mpt=66–67° C.). Microanalysis for $C_{14}H_{17}NO_3$ Calculated C 68.02, H 6.88, N 5.67 Found C 67.92, H 6.90, N 5.63.

(b) 4-[3-(trans-3-aminocyclobutyl)-1H-indol-5-ylmethyl-(4S)-oxazolidin-2-one

The appropriate hydrazine (6.3 g, 30 mmol) and trans-N-(benzyloxycarbonyl)cyclobutanamine-3-acetaldehyde (6.3 g, 25.5 mmol) were heated to 80° C. for 7 hours in 1% sulphuric acid (aq) (100 ml) and ethanol (150 ml). The reaction mixture was evaporated in vacuo and brine added. Extraction with ethyl acetate gave the crude product (10.5 g, 83%) MS (FAB) 420 $(M+1)^+$.

The product from the above was refluxed in 10% formic acid-methanol with palladium hydroxide on carbon (1 g) for 7 hours. The solvent was removed in vacuo and brine added The solution was then washed with ethyl acetate and then made basic (pH 10–12) with dil. ammonium hydroxide solution. Extraction with THF gave the crude product which was purified by flash chromatography (2:14:84 $NH_3$, $ETOH_3$) (2 g, 28%) MS (FAB) 286 $(M+1)^+$.

(c) Trans4-[3-(3-dimethylaminocyclobutyl)-5-indolylmethyl]-(S)-1,3-oxazolidin-2-one Formaldehyde (0.18 ml, 2,22 mmol) in methanol (5 ml) was added to the product of step (b) (250 mg, 0.88 mmol), acetic acid (0.26 ml, 4.55 mmol) and sodium cyanoborohydride (70 mg, 1.17 mmol) in methanol (15 ml) and stirred at room temperature under a nitrogen atmosphere overnight.

Water was added and the mixture washed with ethylacetate. The aqueous phase was then adjusted to pH 10 with potassium carbonate and saturated with sodium chloride.

Extraction with ethylacetate gave a sticky gum which was chromatographed on silica eluting with 1% 0.88 $NH_3$ solution in methanol (r.f~0.4) to give an off white powder. Elemental analysis for $C_{18} H_{23} N_3 O_2$ 0.35 $CHCl_3$ Calculated C 62.05, H 6.63, N 11.83 Found C 62.21, H 6.76, N 11.55 mpt=Becomes gummy at 77–78° C.

This solvated compound can be dried in vacuo at 80° C. to provide the anhydrous compound of Example 4.

The following compounds were made by selecting appropriate starting materials and following the method described in Example 2.

| Example No. | W | | n | A | R | $R^1$ | isomer |
|---|---|---|---|---|---|---|---|
| 3. Melting point 197–199° C. | 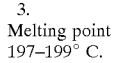 | | 2 | cyclobutyl | Me | Me | trans |
| 4. M. pt. 159–160° C. | 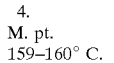 | | 1 | cyclobutyl | Me | Me | (S) trans |
| 5. M. pt. 67–69° C. | 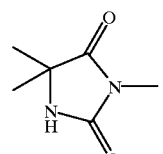 | | 2 | cyclobutyl | Me | Me | trans |

-continued

| Example No. | W | n | A | R | R¹ isomer |
|---|---|---|---|---|---|
| 6. M. pt. 85–87° C. | 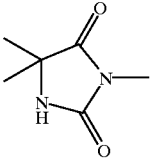 | 2 | cyclobutyl | H | H trans |
| 7. M. pt. 52–53° C. | 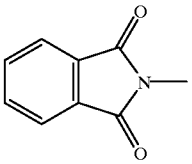 | 2 | cyclobutyl | Me | Me trans |
| 8. M. pt. 66–68° C. | 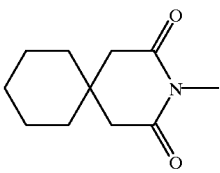 | 2 | cyclobutyl | Me | Me trans |
| 9. M. pt. 106–109° C. dec. | 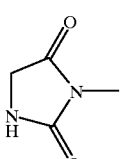 | 1 | cyclobutyl | Me | Me trans |
| 10. M. pt. 220–222° C. □ | SO₂NHMe | 1 | cyclobutyl | Me | Me trans |
| 11. M. pt. 163–165° C. | 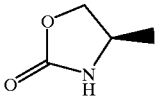 | 1 | cyclobutyl | Me | Me (R) trans |
| 12. M. pt. 70–72° C. | 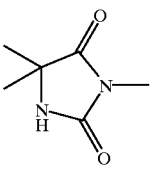 | 1 | cyclobutyl | Me | Me trans |
| 13. M. pt. foam | 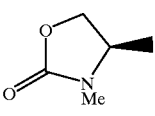 | 1 | cyclobutyl | Me | Me (R)-trans |
| 14. M. pt. 93–95° C. | CONH₂ | 0 | cyclobutyl | Me | Me trans |
| 15. Hygrogscopic | 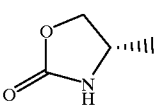 | 1 | cyclobutyl | Me | Me (S)-cis |
| 16. | OPh | 0 | cyclobutyl | H | H trans |

-continued

| Example No. | W | n | A | R | R¹ | isomer |
|---|---|---|---|---|---|---|
| 17. M. pt. 164–166° C. | OPh | 0 | | cyclobutyl | Me | Me trans |
| 18. M. pt. 189–190° C. | | 0 | 4-methyl-2-methyl-1,3,4-oxadiazole | cyclobutyl | Me | Me trans |
| 19. M. pt. foam | | 1 | (4S)-3-methyl-2-oxo-oxazolidin-4-yl | methyl cyclobutyl | Me | Me (S) trans |

EXAMPLE 20

Alternative synthesis for 4-[3-(Trans-3-aminocyclobutyl)-5-indolylmethyl-] (4S)-oxazolidin-2-one: Compound of Example 1

The trans-N-(benzyloxycarbonyl)-cyclobutanamine-3-acetaldehyde (1 g, 4 mmol) and hydrazine (1.2 g, 5.8 mmol) were heated to 80° C. in 1% aqueous sulphuric acid (50 ml) for 6 hours. After cooling the solid was filtered off and dried under vacuum. Used crude for next stage. mpt=95–100° C. The Cbz protected indole (500 mg, 1.2 mmol) and palladium hydroxide on carbon (50 mg, 0.36 mmol) were refluxed in 10% formic acid in methanol (25 ml) for 3 hours. The catalyst was filtered off and the solvent evaporated under reduced pressure. Brine was added to the residue and the pH adjusted to 11 with 0.88 ammonium solution. The milky solution was extracted with tetrahydrofuran, dried over $MgSO_4$ and evaporated under vacuum to give the free base as a foam. HRMS Calculated 285.1477. Found 285.1485.

EXAMPLE 21

(+)-5-[3-trans-3-dimethylaminocyclobutyl -1H-indol-5-lmethyl]oxazolidin-2-one (a) 5-benzyl-2-oxazolidinone 2,3-Epoxypropylbenzene (60 g, 448 mmol) and potassium cyanate (70 g, 364 mmol) were refluxed in DMF (600 ml) and water (300 ml) for 4 hours. The solvent was evaporated in vacuo and water added. The aqueous was then extracted with ethyl acetate, dried (Mg $SO_4$) and evaporated. Recrystallization from ethyl acetate gave the product (28.2 g, 36%) Mpt 106–107° C. MS (EI) 177 (M+), 133, 86.

(b) 5-(4-nitrobenzyl)-2-oxazolidinone 4-benzyl-2-oxazolidinone (5 g, 28 mmol), potassium nitrate (2.9 g, 29 mmol) and p-iodotoleune (0.5 g, 2 mmol) were stirred in trifluoracetic acid (50 ml) overnight. The mixture was then poured onto ice and extracted with ethyl acetate. This was washed with sodium bicarbonate solution, dried (Mg $SO_4$) and evaporated. Flash chromatography (70:30 ethyl acetate/hexane) gave the product (2.2 g, 35%) Mpt 150–151° C., MS (ES) 223 (M+1)+

(c) 5-(4-aminobenzyl)-2-oxazolidinone 4-(4-nitrobenzyl)-2-oxazolidone (9.9 g, 45 mmol) and 10% palladium on carbon (900 mg) were stirred under a hydrogen atmosphere in methanol (200 ml) and 2.5N aq. HCl (50 ml) at room temperature for 4 hours. The reaction mixture was filtered and evaporated. Water was added and the solution washed with ethyl acetate. The aqueous phase was then basified with dil NaOH solution and extracted with THF to give the crude product (6.2 g, 72%) Mpt 135–138° C. MS(EI) 192 (M+), 106, The 5-(4-aminobenzyl)-2-oxazolidinone (1.7 g, 8.9 mmol) was disolved in c.HCl (2 ml) and water (7.5 ml) and then cooled to below 5° C. A solution of sodium nitrite (0.61 g 7 mmol) in water (7.7 ml) was then added dropwise. The solution was then stirred at ~5° C. for 20 minutes. This was then added slowly to a cooled solution (below 5° C.) of sodium sulphite (3.4 g, 27 mmol) in water (15 ml). The solution was stirred for 20 minutes before allowing it to warm to room temperature and then heating slowly to 60° C. c.HCl (3 ml) was then added and heating at 60° C. continued overnight. The solution was then diluted with water (15 ml) and ethanol (30 ml). Trans-N-(benzyloxycarbonyl) cyclobutanamine-3-acetaldehyde (1.5 g, 6 mmol) was then added and the mixture heated to 80° C. for 7 hours. Partial evaporation followed by extraction with THF gave the crude product which was purified by flash chromatography (5:95 methanol/chloroform) (1.7 g, 46%) MS (FAB) 420 (M+1)+

The product of this step was then treated by methods outlined in example 2 to provide (±-5-[3-(trans-3-dimethylaminocyclobutyl)-1H-indol-5-ylmethyl] oxazolidin-2-one.

EXAMPLE 22

4-[3-(3-methylaminocyclobutyl)-1H-indol-5-ylmethyl]-(4S)-oxazolidin-2-one (a) Trans-N-(benzyloxycarbonyl) cyclobutanamine-3-acetaldehyde diethyl acetal.

Trans-N-(benzyloxycarbonyl)cyclobutanamine-3-acetaldehyde (1 g, 4 mmol), triethylorthoformate (1.35 ml, 8 mmol) and p-toluene sulphonic acid (100 mg) were refluxed in ethanol for 3 hours. The reaction mixture was evaporated in vacuo and purified by flash chromatography (10:90 Ethyl acetate/cyclohexanone) to give a colourless oil (1.2 g, 94%).

(b) Trans-N-benzyloxycarbonyl-N-methyl cyclobutanamine-3-acetaldehyde diethyl acetal.

Trans-N-(benzyloxycarbonyl) cyclobutanamine-3-acetaldehyde diethyl acetal (1.2 g, 3.7 mmol) in dry DMF(10 ml) was added dropwise to a cold suspension of sodium hydride (60% in oil) (165 mg, 4.1 mmol) in dry DMF (10 ml). After the addition was complete the mixture was allowed to stirred at 10° C. for ½ hour. Methyl iodide (0.23 ml, 3.7 mmol) in dry DMF (5 ml) was then added dropwise. The mixture was then allowed to warm to room temperature and stir for 2 hours. The reaction was then poured onto ice and extracted with ether. Flash chromatography (10:90 ethylacetate/cyclohexane) gave the product as a colourless oil (1 g, 83%).

The product of this step was then treated by methods outlined in example 2 to provide 4-[3-(trans-3-methylaminocyclobutyl)-1H-indol-5-ylmethyl]-(4S) oxazolidin-2-one.

EXAMPLE 23

5-N-benzylcarboxamido-3-trans-3-dimethylaminocyclobutyl)-1H-indole (a) 3-(trans-3-dimethylaminocyclobutyl)1H-indole-5-carboxylic acid.

5-carboxamido-3-(trans-3-dimethylaminocyclobutyl)-1H-indole (0.4 g, 1.6 mmol), prepared using the methods described in example 2, was refluxed in 10M NaOH solution (15 ml) and methanol (10 ml) for 7 hours. The resulting solution was cooled in ice and neutralized with dil HCl. This was then evaporated to dryness in vacuo and methanol added. The sodium chloride was filtered off and the solution evaporated to give the crude product.

(b) 5-N-benzylcarboxamido-3-trans-3-dimethylaminocyclobutyl)-1H-indole

The crude 3-(trans-3-dimethylaminocyclobutyl)-1H-indole-5-carboxylic acid (0.4 g, 1.6 mmol), 0-(1H-benzotriazol-1-yl)-N,N,N$^1$N$^1$-tetramethyluronium tetrafluoroborate (0.57 g, 1.8 mmol), benzylamine (0.18 ml, 1.6 mmol) and triethylamine (0.25, 1.8 mmol) were stirred at room temperature in dry DMF (15 ml) for 5 hours. The reaction was quenched with water and extracted with ethyl acetate. This was dried (MgSO$_4$) and evaporated to give the crude product which was purified by flash chromatography (1:10:89 0.88 NH$_3$, MeOH, CHCl$_3$) (175 mg, 32%) MS(EI) 347 (M+).

EXAMPLE 24

2-{2-[3-(trans-3-dimethylaminocyclobutyl)-1H-indol-5-yl]ethyl} phthalamide

The Cbz protected intermediate prepared by methods described in example 2, (0.5 g, 1.6 mmol), boron trifluoride etherate (2 ml, 16 mmol) and ethylmercaptan (3.4 ml, 46 mmol) were refluxed for 48 hours. The mixture was then evaporated in vacuo and brine added. The pH was then adjusted to pH 10–12 with dil NaOH solution. Extraction with THF gave the crude product which was chromatographed on silica eluting with 1:99 0.88 NH$_3$/MeOH. (190 mg, 33%) MS (FAB) 360 (M+1)$^+$.

The product of this step was then treated by methods outlined in example 2 to provide 2-{2-[3-(trans-3-dimethylaminocyclobutyl)-1H-indol-5-yl]ethyl} phthalamide.

EXAMPLE 25

3-[trans-3-dimethylaminocyclobutyl]-1H-indol-5-yl acetamide (a) 4-hydrazinophenylacetic acid hydrochloride.

To a solution containing conc. HCl (76 ml) and 4-amino phenylacetic acid (10 g: 66 mmol) at 4° C. was added a solution of sodium nitrite (4.56 g; 55 mmol) in water (10 ml) dropwise, while maintaining the temperature at 0 to 4° C. The mixture was stirred for 30 minutes and added to a cold (0° C.) solution of SnCl$_2$ (74.5 g 331 mmol) in conc. HCl (50 ml). The mixture was left to warm to room temperature overnight. The precipitate formed was filtered and washed with water (50 ml), 50% aq.HCl (50 ml), water (50 ml) and ether (2×50 ml). The solid was dried in vacuo to give the product 13 g. M.pt. 220–223° C. dec.

MS. 166(M+) 151, 135, 121; NMR [360 Mz, $^1$H] ppm 3.5 (s, 2H) 6.9 (d, 2H) 7.1 (d, 2H), 10.7 (bs).

(b) 3-[trans-N-(benzyloxycarbonyl)-3-aminocyclobutyl]-1H-indol-5-yl acetic acid.

To 4-hydrazinophenylacetic HCl. in 1% aq. sulphuric acid (75 ml) was added trans-N-(benzyloxycarbonyl) cyclobutanamine-3-acetaldehyde (5 g, 20 mmol). The mixture was heated to 90° C. for 7 hours. The semi-solid formed was filtered and washed with 1% H$_2$SO$_4$ and water. The solid was then taken up into ethyl acetate and washed with water. The organic phase was dried (MgSO$_4$). The product was obtained as a sticky solid. Yield: 6.5 g (74%).

(c) 3-[trans-N-(benzyloxycarbonyl)-3-aminocyclobutyl]-1H-indole-5-ylacetamide.

To a solution of 3-[trans-N-(benzyloxycarbonyl) cyclobutanamine]-1H-indol-5-yl acetic acid (0.5 g, 1.38 mmol) in DMF (5 ml) was added 0-(3,4-dihydro4-oxo-1,2,3-benzotriazine-3-yl)N,N,N$^1$,N$^1$-tetramethyluronium tetrafluoroborate [TBTU] (0.44 g; 1.38 mmol) and Et$^3$N (0.21 ml: 1.52 mmol). Anhydrous ammonia was then bubbled through the solution for 1 hour at room temperature with cooling in ice as necessary. The mixture was stirred overnight at room temperature. The solvent was evaporated under vacuum. The residue was chromatographed on silica using MeOH (10%)/chloroform (89%)/880 NH$_3$ (11%). Yield 0.28 g (56%) MS 269, 253, 182 NMR [360MH$_3$, H$^1$] 2.49 (t, 4H) 3.3 (m, 2H), 3.55 (m 1H) 4.11 (m 1H); 5.0 (m 3H), 6.78 (bs 1H), 6.98 (dd 1.6 HZ, 8.5 HZ; 1H) 7.3 (m.9) 7.7 (d 6.8 HZ, 1H). The product of this step was then treated by methods outlined in example 2 to provide 3-[trans-3-dimethylaminocyclobutyl]-1H-indol-5-yl acetamide.

EXAMPLE 26

N-benzyl-3-[trans-3-dimethylaminocyclobutyl]-1H-indol-5-yl acetamide.

(a) N-benzyl-3-[trans-3-(benzyloxycarbonylamino) cyclobutyl]-1H-indol-5-yl acetamide To a solution of 3-[trans-N-(benzyloxycarbonyl)-3-aminocyclobutyl]indol-5-yl acetic acid (1 g, 2.76 mmol) in DMF (5 ml) was added TBTU (0.97 g 3.04 mmol), Et$_3$N (0.42 ml 3.04 mmol) and benzylamine (0.33 ml 3.04 mmol). The mixture was stirred overnight at room temperature. The solvent was evaporated under vacuum and the residue chromatographed on Silica 5% MeOH/94% CHCl$_3$/1% 880 NH3 to give a pale yellow oil. yield: 0.81 g (80%) MS 468 (M+1), 392, 333.

The product of this step was then treated by methods outlined in example 2 to provide N-benyl-3-[trans-3-dimethylaminocyclobutyl]-1H-indol-5-yl acetamide.

EXAMPLE 27

3-methyl-5-[3-(trans-3-dimethylaminocyclobutyl)-1H-indol-5-ylmethyl] 1,2,4-oxadiazole.

(a) N-[(dimethylamino)ethylidene]-3-[trans-3-(benzyloxycarbonylamino)cyclobutyl]-1H-indol-5-ylacetamide.

To a solution containing 3-[trans-N-benzyloxycarbonyl-3-aminocyclobutyl]indol-5-yl acetamide (4.68 g 13 mmol)

in toluene (10 ml) was added N,N-dimethyl acetamide dimethyl acetal (40 ml). The mixture was then heated at 120° C. for 2 hours under Dean & Stark conditions. The solution becomes very dark. The solvent is evaporated under vacuum to give N-[(dimethylamino)ethanylidene]-3-[trans-3-(benzyloxycarbonylamino)cyclobutyl]-1H-indol-5-ylacetamide.

Yield: 5.7 g crude.

(b) 5-{3-[N-(benzyloxycarbonyl)-trans-3-dimethylaminocyclobutyl]-1H-indol-5-yl}-3-methyl-1,2,4-oxadiazole To a mixture containing hydroxylamine HCl, (10 mg 1.6 mmol) 5N NaOH (0.2 ml), p-dioxane (3 ml) and 70% acetic acid (10 ml) was added the amidine (500 mg 1.6 mmol) and the mixture heated to 120° C. for 1 ½ hours. The solvent was evaporated under vacuum and the residue was chromatographed using silica and 40% EtOAc/60% cyclohexane to give the product.

Yield: 150 mg (31%) as a foam; MS 417 (M+1) 296

The product of this step was then treated by methods outlined in example 2 to provide 3-methyl-5-[3-(trans-3-dimethylaminocyclobutyl)-1H-indol-5-ylmethyl]-1,2,4-oxadiazole.

EXAMPLE 28

3-methyl-5-[3-(trans-3-dimethylaminocyclobutyl)-1H-indol-5-ylmethl]1,2,4-triazole.

(a) To a solution of the amidine, prepared as in example 35 (a) above, (3 g, 6.99 mmol) in 70% aqueous acetic acid (100 ml), was added hydrazine hydrate 10.9 ml, 8.39 mmol). The mixture was stirred at 90° C. for 5 hours. The mixture was concentrated under reduced pressure and diluted with water (100 ml). The aqueous phase was extracted with ethyl acetate (2×50 ml). The organic phase was dried (MgSO$_4$) and evaporated. The residue was chromatographed using 10% MeOH/89% CHCl$_3$/%NH$_3$ to give an oil.

Yield: 200 mg MS 416 (M+1), 415 (M$^+$) 326

The product of this step was then treated by methods outlined in example 2 to provide 3-methyl-5-[3-(trans-3-dimethylaminocyclobutyl)-1H-indol-5-ylmethyl]-1,2,4-triazole.

EXAMPLE 29

(S)-2-(5-(2-Oxo4-oxazolidinylmethyl)-1H-indol-3-yl)cyclopropylamine a) Ethyl 2-ethenylcyclopropane carboxylate Butadiene (200 ml, Aldrich) condensed at −70° was transferred to a glass lined autoclave vessel and ethyl diazoacetate (20 g, 0.175 mol, Aldrich) and rhodium acetate dimer (0.3 g, Aldrich) added. The suspension was stirred in a sealed autoclave for 24 hours at ambient temperature. The contents were diluted with 2% diethyl ether in pentane and passed through a silica pad (50 g). The pad was washed with a little ethanol and further ether-pentane. The eluant containing ethanol was treated separately. The organic phases were concentrated at reduced pressure (<5°) and subjected to short path bulb to bulb disillation (90–105° at 12 mm) to give the product as a colourless liquid (14.6 g).

b) 2-Ethylenecyclopropanecarboxylic acid

The above ester (11.79 g, 84.21 mmol) was dissolved in tetrahydrofaran (THF) (16 ml) and treated with potassium hydroxide (7.32 g) in water (75 ml) and heated under gentle reflux for 5 hours. The reaction mixture was concentrated and the residue dissolved in water. This was acidified with conc. hydrochloric acid to pH 4 and the emulsion was extracted with diethyl ether. The organic phase was dried, concentrated and the residual oil distilled (100–120° at 3 mm) to give the product as a colourless liquid (8.7 g).

c) trans-N-t-Butoxycarbonyl-2-ethenylcyclopropylamine

The above acid (8.66 g, 77.43 mmol) was dissolved in anhydrous toluene (40 ml), cooled to 0°, treated with dry triethylamine (11.9 ml) and then, dropwise, with diphenylphosphoryl azide (23.4 g, Aldrich) in toluene (25 ml). The solution was warmed to 80° and kept at 80–85° for 45 mins. Anhydrous t-butanol (36 ml) and toluene (10 ml) were added quickly and the solution heated at 102° for 6 hours. The reaction mixture was allowed to cool and diluted with diethyl ether, washed with 1N orthophosphoric acid (100 ml), saturated aq.sodium bicarbonate and brine, dried and concentrated. The residual oil was purified by chromatography (silica: 350 g; hexane: ethyl acetate 95:5) to give the product as a colourless oil (3.91 g).

d) trans-N-t-Butoxycarbonyl-2-(2-hydroxyethyl)cyclopropylamine

The above alkene (3.91 g, 21.37 mmol) in anhydrous THF (20 ml) was cooled to 0° and treated with borane: THF complex (42.7 ml, 1M in THF, Aldrich). Stirred at 0° for 2.5 hours then allowed to reach ambient temperature, recooled to −5° and treated sequentially with 6N aq.sodium hydroxide (24.8 ml) and 30% aq. hydrogen peroxide (7.53 ml). The mixture was stirred at room temperature for 10 mins then treated with excess solid potassium carbonate and extracted with ethyl acetate (3×100 ml). The organic phase was washed once with aq. orthophosphoric acid, aq. sodium bicarbonate, brine and dried. The solvent was removed and residual oil subjected to chromatography (silica: 300 g; 1% to 4% methanol in dichloromethane) to give the product as an oil which crystallised upon standing at 3° (4.1 g).

e) trans-N-t-Butoxycarbonyl-2-(2-oxo-ethyl)cyclopropylamine

Oxalyl chloride (175 ml) in dry dichloromethane (DCM (8 ml) was cooled to −65° and treated with dimethyl sulphoxide (316 mg) in DCM (1 ml) and after 10 mins. the above alcohol (394 mg, 1.96 mmol) in DCM (2 ml) was added. After 1 hour at −65° triethylamine (1.1 ml) was added and reaction allowed to reach 0° and diluted with diethyl ether (25 ml). The organic phase was washed with water, 1N orthophosphoric acid, satd.aq. sodium bicarbonate and brine and dried. The solvents were removed to give the product as a pale yellow oil (349 mg).

f) (S)-2-(5-(2-Oxo-4-oxazolidinylmethyl)-1H-indol-3-yl)cyclopropylamine

The above aldehyde (349 mg, 1.75 mmol) was treated with 3:1 water: acetic acid (25 ml) and (S)-4-(2-oxo-4-oxazolidinylmethyl)phenylhydrazine (440 mg, 2.12 mmol). The mixture was heated under nitrogen at 80–85° for 5 hours. The reaction mixture was concentrated, DCM, ethanol, 880 ammonia (85:15:1) added and reconcentrated. The residue was subjected to chromatography (silica: 50 g; DCM, ethanol, ammonia (85:15:1) and the component (R$_f$ 0.10, silica-DCM, methanol, ammonia (90:10:1) isolated. The latter was subjected to purification (×2) by preparative HPLC (Zorbax C$_8$, MeCN—0.1M aq.NH$_4$OAc) to give the title compound as a yellow foam in the form of an acetate salt.

7.45(1H,s,2-H); 7.70 (1H,s,NH); 10.57 (1H,s,indole NH). Accurate mass; 271.13208 (C$_{15}$H$_{17}$N$_3$O$_2$)

PHARMACEUTICAL FORMULATION EXAMPLES

In the following Examples, the "active ingredient" may be any compound of formula (I) or (Ia) and/or a physiologically acceptable salt, solvate, or physiologically functional derivative thereof.

(1) Tablet formulations
(i) Oral

|  | Mg/tablet | |
|---|---|---|
|  | A | B |
| Active ingredient | 2.5 | 2.5 |
| Avicel | 13 | — |
| Lactose | 100.5 | 69.5 |
| Starch (maize) | — | 9 |
| Sodium starch glycollate | 5 | — |
| Povidone | 3 | 3 |
| Magnesium stearate | 1 | 1 |
|  | 125 | 85 |

Formulations A to C may be prepared by wet granulation of the first six ingredients with the povidone, followed by addition of the magnesium stearate and compression.

(ii) Buccal

|  | Mg/tablet |
|---|---|
| Active ingredient | 2.5 |
| Hydroxypropylmethyl cellulose (HPMC) | 35 |
| Polycarbophil | 51.5 |
| Magnesium stearate | 1 |
|  | 90 |

The formulation may be prepared by direct compression of the admixed ingredients.

(2) Capsule formulations
(i) Powder

|  | Mg/Capsule | |
|---|---|---|
|  | D | E |
| Active ingredient | 2.5 | 2.5 |
| Lactose | 175.5 | — |
| Starch (1500 NF) | 45 | 139.5 |
| Sodium starch glycollate | — | 6 |
| Magnesium stearate | 2 | 2 |
|  | 225 | 150 |

Formulations D and E may be prepared by admixing the ingredients and filling two-part hard gelatin capsules with the resulting mixture.

(i) Liquid fill

|  | Mg/Capsule | |
|---|---|---|
|  | F | G |
| Active ingredient | 2.5 | 2.5 |
| Macrogol 4000 BP | 222.5 | — |
| Lecithin | — | 110 |
| Arachis Oil | — | 112.5 |
|  | 225 | 225 |

Formulation F may be prepared by melting the Macrogol 4000 BP, dispersing the active ingredient in the melt and filling two-part hard gelatin capsules therewith. Formulation G may be prepared by dispersing the active ingredient in the lecithin and arachis oil and filling soft, elastic gelatin capsules with the dispersion.

(iii) Controlled release

|  | Mg/tablet |
|---|---|
| Active ingredient | 2.5 |
| Avicel | 145.5 |
| Lactose | 62 |
| Triethylcitrate | 3 |
| Ethyl cellulose | 12 |
|  | 225 |

The formulation may be prepared by mixing and extruding the first four ingredients and spheronising and drying the extrudate. The dried pellets are coated with ethyl cellulose as a release controlling membrane and filled into two-part, hard gelatin capsules.

(3) Intravenous injection formulation

|  | % by weight |
|---|---|
| Active ingredient | 2% |
| Hydrochloric acid) Citrate buffer) | q.s to pH 7 |
| Water for injections | to 100% |

The active ingredient is taken up in the citrate buffer and sufficient hydrochloric acid added to affect solution and adjust the pH to 7. The resulting solution is made up to volume and filtered through a micropore filter into sterile glass vials which are sealed and oversealed.

Biological Assays

A: Rabbit Saphenous Vein Assay

Compounds of formula (I) prepared in Synthetic Examples 1 to 17 were each tested for their activity as agonists for their activity as agonists for the "5-HT$_1$-like" receptor mediating smooth muscle contraction by the following method.

Right and left lateral saphenous veins were obtained from male New Zealand White Rabbits (2.4–2.7 kg) which had been killed by intravenous injection of pentobarbitone sodium (60 mg/kg). Ring segments (3–5 mm wide) prepared from each vessel were suspended between two wire hooks and immersed in 20 ml organ baths containing Krebs' solution (pH 7.4) of the following composition (mM): NaCl 118.41, NaHCO$_3$ 25.00, KCl 4.75, KH$_2$PO$_4$ 1.19, MgSO$_4$ 1.19, glucose 11.10 and CaCl$_2$ 2.50. Cocaine (30 $\mu$M) was present in the Krebs' solution throughout the experiment to prevent the uptake of amines by sympathetic neurones. The Krebs' solution was maintained at 37° C. and continually gassed with 95% oxygen/5% carbon dioxide. Increases in tissue isometric force were measure using Grass FT03C force displacement transducers and recorded on a Gould BD-212 pen recorder.

A force of 1.0 g was applied to each preparation and re-established twice during a subsequent period of 30 minutes. During this period, tissues were exposed to pargyline (500 $\mu$M to irreversibly inhibit monoamine oxidase and to phenoxybenzamie (0.1 $\mu$M to inactivate $\alpha_1$-adrenoceptors. At the end of the 30 minutes, the inhibitors were removed by several changes he organ bath Krebs' solution.

Agonist activity was assessed by simulative additions of the test compound, its concentration being increased in 0.5 log$_{10}$ unit increments until further additions caused no further change in tissue force. In each experiment, the activity of the test compound was compared to the activity of 5-HT. Activity was expressed in terms of the p(A$_{50}$] (–log$_{10}$[M] where M is the molar concentration of agonist required to produce half the maximum effect). Where the compounds were found to be antagonists, the results are expressed as pKb. The results obtained for the compounds of Synthetic Examples 1 to 19 and 21 to 28 are shown in Table 1.

TABLE 1

| Example | pA$_{50}$ (α) | pKb |
|---|---|---|
| 1 (tran) | 6.42 (0.78) | |
| 1 (cis) | 5.8 (0.76) | |
| 3 | | 5.72 |
| 4 | 5.72 (0.09) | |
| 5 | | 6.05 |
| 6 | | 5.57 |
| 7 | | 6.77 |
| 8 | | 7.18 |
| 9 | | 5.03 |
| 10 | | 5.25 |
| 11 | | 4.95 |
| 12 | | 6.23 |
| 13 | 4.85 (0.38) | |
| 14 | 6.25 (0.52) | |
| 15 | 5.15 (0.29) | |
| 16 | | <6.5 |
| 17 | | 6.62 |
| 18 | | 6.02 |
| 19 | | 5.73 |
| 21 | 5.44 (0.16) | |
| 22 | 6.15 (0.72) | |
| 23 | | 5.90 |
| 24 | 5.21 (0.48) | |
| 25 | | 4.78 |
| 26 | | 5.41 |
| 27 | | 3.12 |
| 28 | | 5.18 |

Calf Caudate Assay

Compounds of formula (I) prepared in Synthetic Examples 1 to were further tested for their activity as agonist for the "5-HT$_1$-like" receptor mediating smooth muscle contraction by the following method Membranes were prepared from homogenates of calf caudate nucleus. Competition binding studies were performed with 3.5 nM [$^3$H]-5HT (approx. 25 Ciml$^{-1}$) in the presence of 15 μM mesulergine and 15 μM 8-OH-DPAT, using 5 mg wet weight ml$^{-1}$ of membranes in a total volume of 1 ml per tube. Binding data was fitted to a four parameter logistic function to obtain estimates of pIC$_{50}$. These were converted to pK: values using the Cheng-Prussof equation.

The results obtained for the compounds of Synthetic Examples 1 and 2 are shown in Table 2.

TABLE 2

| Example | Activity P[A$_{50}$] |
|---|---|
| 1 | 7.8 |
| 2 | 7.05 |

We claim:
1. A compound of formula (I)

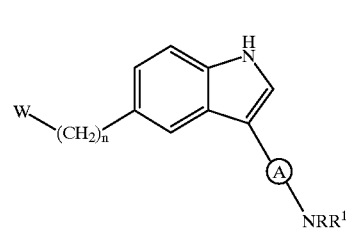

wherein
R and R$^1$ are each independently hydrogen or C$_{1-4}$ alkyl or R and R$^1$ are linked to form an azetidine ring;
A is C$_{3-6}$ cycloalkyl or C$_{1-3}$ alkyl-C$_{3-6}$ cycloalkyl;
n is an integer of from 0 to 3;
W is a group (i) or (ii):

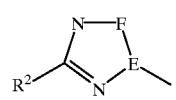

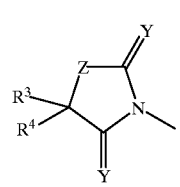

wherein
R$^2$ is hydrogen or NR$^5$R$^6$, wherein R$^5$ and R$^6$ are hydrogen or C$_{1-4}$ alkyl;
E is —C═;
F is ═C—;
R$^3$ and R$^4$ are hydrogen or C$_{1-4}$ alkyl;
Y is oxygen or sulphur;
Z is —NH— or —S—;
or a salt, solvate or physiologically functional derivative thereof.

2. A compound as defined in claim 1 wherein:
R and R$^1$ are each independently hydrogen or C$_{1-4}$ alkyl;
A is C$_{3-6}$ cycloalkyl;
or a salt, solvate or physiologically functional derivative thereof.

3. A compound according to claim 1 or 2 of formula (Ia):

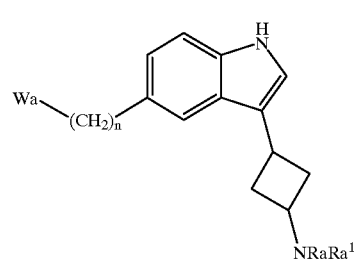

wherein
Ra and Ra$^1$ are each independently hydrogen or C$_{1-4}$ alkyl;

n is an integer of from 0 to 3;
Wa is a group (i) or (ii):

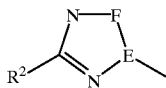  (i)

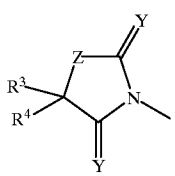  (ii)

wherein
R² is hydrogen or NR⁵R⁶, wherein R⁵ and R⁶ are hydrogen or $C_{1-4}$ alkyl;
E is —C≡;
F is ≡C—;
R³ and R⁴ are hydrogen or $C_{1-4}$ alkyl;
Y is oxygen or sulphur;
Z is —NH— or —S—,
or a salt, solvate or physiologically functional derivative thereof.

4. A compound selected from the group consisting of:
5-(5,5-dimethyl)-3-{2-[3-trans-3-dimethylaminocyclobutyl)-1H-indol-5-yl]ethyl}imidazole din-2,4-dione, 3-{2-[3-(trans-3-dimethylaminocyclobutyl)-1H-indol-5-yl]ethyl}imidazolidin-2,4-dione, 3-{2-[3-(trans-3-aminocyclobutyl)-1H-indol-5-yl]ethyl}-5,5-dimethylimidazolidin-2,4-dione, 5,5-dimethyl-3-[3-(trans-3-dimethylaminocyclobutyl)-1H-indol-5-ylmethyl]imidazolidin-2,4-dione, 3-[3-(trans-3-dimethylaminocyclobutyl)-1H-indol-5-ylmethyl]imidazolidin-2,4-dione.

5. A pharmaceutical composition comprising as active ingredient at least one compound of claim 1 or a pharmacologically acceptable salt or solvate thereof together with at least one pharmaceutically acceptable carrier or excipient.

6. A method for the prophylaxis or treatment of a clinical condition in a mammal for which a "5-HT₁-like" receptor agonist is indicated which comprises administering a compound of claim 1 in an effective amount.

7. A method according to claim 6 wherein the clinical condition is migraine.

8. A process for the preparation of a compound of claim 1 which process comprises:
(a) reacting a compound of formula (II)

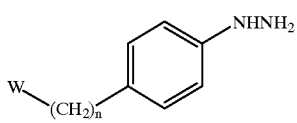  (II)

wherein W and n are as defined in claim 1 with a compound of formula (III)

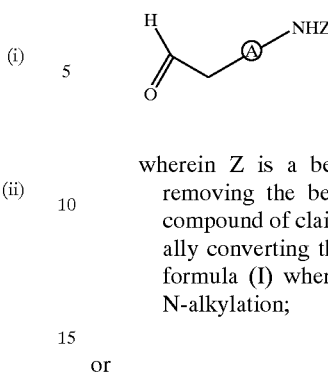  (III)

wherein Z is a benzyloxycarbonyl group and then removing the benzyloxycarbonyl group to give a compound of claim 1 wherein Ra=R¹=H and optionally converting that compound into a compound of formula (I) wherein R and/or R¹ is $C_{1-4}$ alkyl by N-alkylation;

or (b) reacting a compound of formula (II) with a compound of formula (IV)

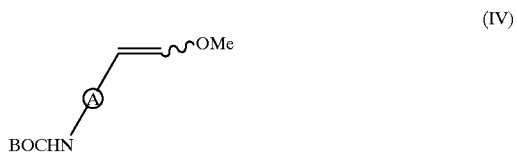  (IV)

wherein BOC is tertiary butoxy carbonyl, to give a compound of formula (I) wherein R=R¹=H and optionally converting that compound into a compound of formula (I) wherein R and/or R¹ is $C_{1-4}$ alkyl by N-alkylation;

or (c) when A is a cyclopropyl group, reacting a compound of formula (II) with a compound of formula (V)

  (V)

wherein BOC is tertiary butoxycarbonyl to give a compound of formula (I) wherein R=R¹=H and optionally converting that compound into a compound of formula (I) wherein R and/or R¹ is $C_{1-4}$ alkyl by N-alkylation.

9. An intermediate compound of formula (III)

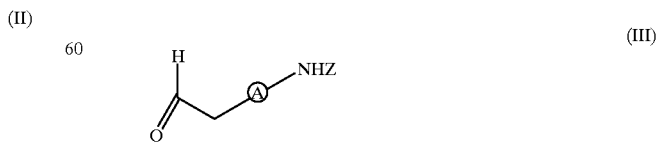  (III)

wherein A and Z are as defined in claim 8.

10. An intermediate compound of formula (IV)
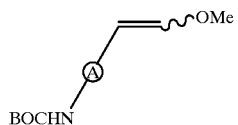
(IV)
wherein A is as defined in claim 8.
11. An intermediate compound of formula (V)
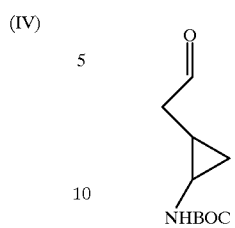
(V)
wherein BOC is as defined in claim 8.
* * * * *